United States Patent
Wells et al.

(10) Patent No.: US 6,768,111 B1
(45) Date of Patent: Jul. 27, 2004

(54) METHOD FOR SEM MEASUREMENT OF TOPOLOGICAL FEATURES

(75) Inventors: Oliver C. Wells, Yorktown Heights, NY (US); Lynne M. Gignac, Beacon, NY (US); Jonathan L. Rullan, Albany, NY (US); Conal E. Murray, Yorktown Heights, NY (US)

(73) Assignee: International Business Machines Corp., Armonk, NY (US)

( * ) Notice: Subject to any disclaimer, the term of this patent is extended or adjusted under 35 U.S.C. 154(b) by 0 days.

(21) Appl. No.: 10/663,552

(22) Filed: Sep. 16, 2003

(51) Int. Cl.[7] .................... G01N 23/00; G01K 7/00
(52) U.S. Cl. ............................. 250/307; 250/311
(58) Field of Search ............................ 250/307, 309, 250/310, 311

(56) References Cited

U.S. PATENT DOCUMENTS

| | | | | |
|---|---|---|---|---|
| 4,683,376 A | * | 7/1987 | Feuerbaum | 250/309 |
| 6,452,176 B1 | * | 9/2002 | Davis | 250/310 |
| 6,566,655 B1 | * | 5/2003 | Choo et al. | 250/310 |
| 2003/0064571 A1 | * | 4/2003 | Takeda et al. | 438/488 |

* cited by examiner

Primary Examiner—Jack Berman
Assistant Examiner—Johnnie L. Smith, II
(74) Attorney, Agent, or Firm—Rodney T Hodgson

(57) ABSTRACT

A method of measurement of topographic features on a surface of a substrate is presented, wherein a focused beam of particles falls onto the surface of the substrate, and backscattered particles are detected with a particle detector. An opaque material is interposed between the surface and the detector, and the position of the shadow of an edge of the opaque material on the detector is recorded. The relative position of the edge and the surface of the substrate is then determined, and the topography of the surface determined as the particle beam and the substrate are moved with respect to one another.

15 Claims, 3 Drawing Sheets

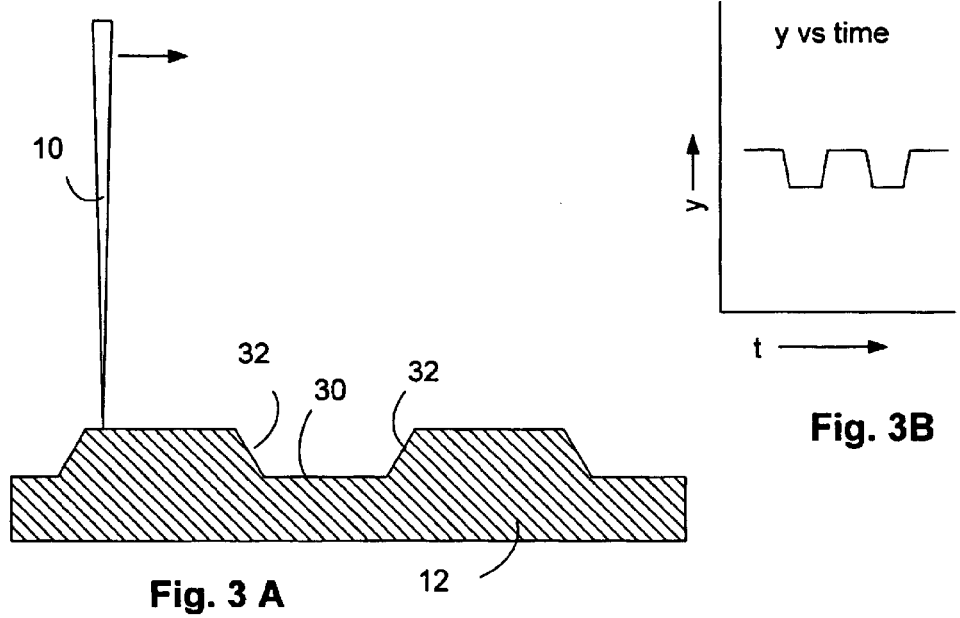
Fig. 3 A
Fig. 3B
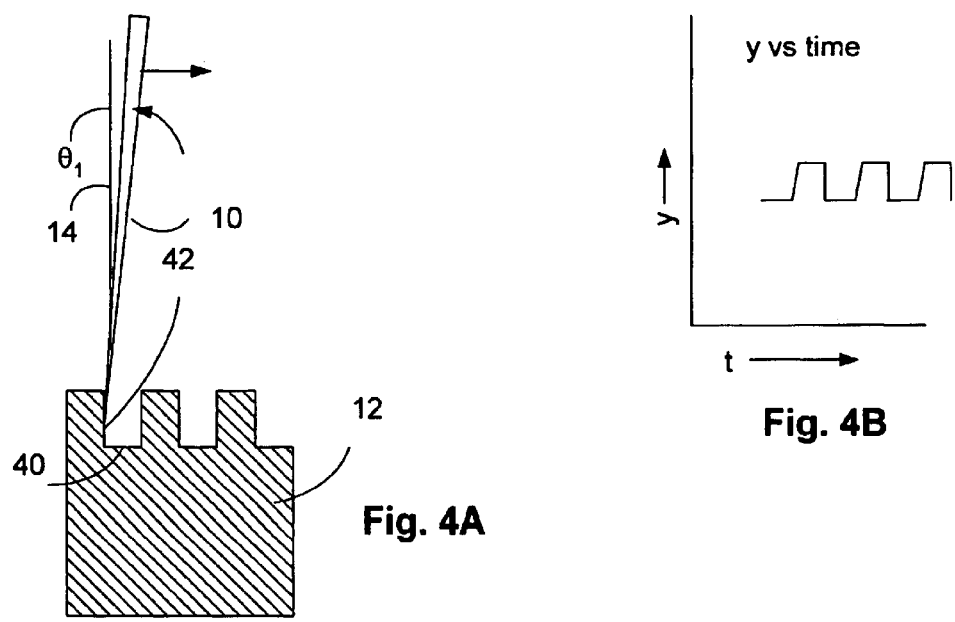
Fig. 4A
Fig. 4B

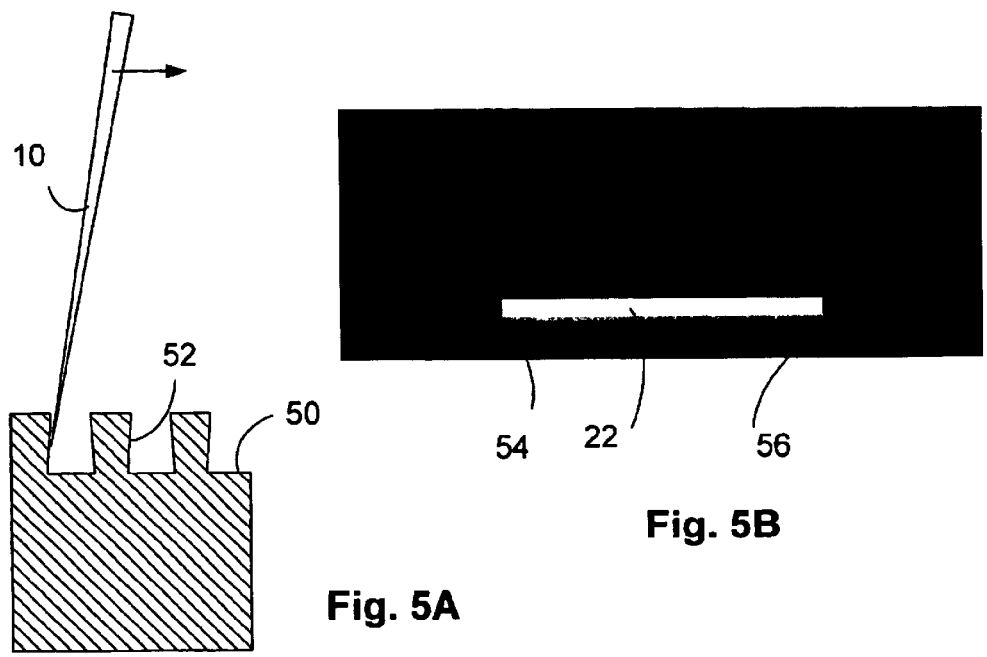
Fig. 5A
Fig. 5B
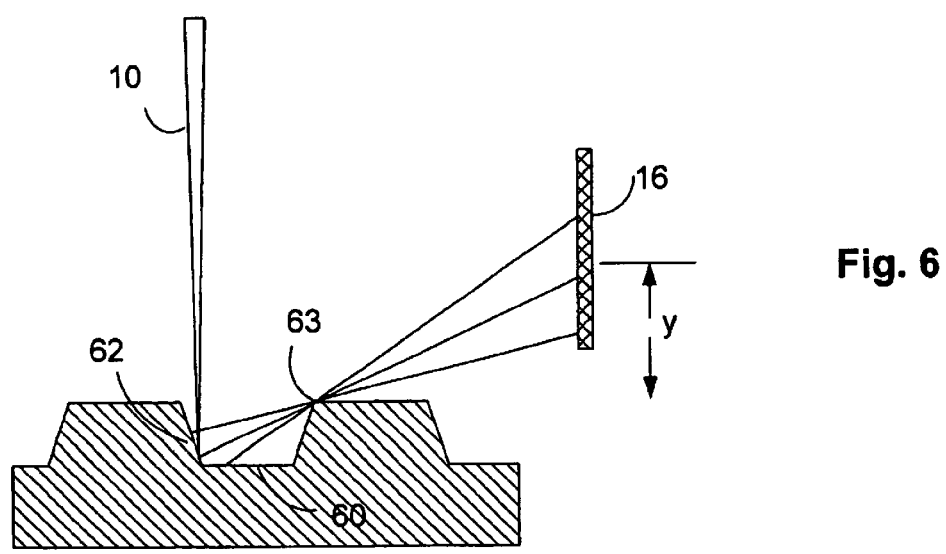
Fig. 6

METHOD FOR SEM MEASUREMENT OF TOPOLOGICAL FEATURES

FIELD OF THE INVENTION

The field of the invention is the field of measurement of topological features on the surface of a substrate, principally but not limited to using focused electron beams and ion beams.

OBJECTS OF THE INVENTION

It is an object of the invention to produce a method of determining the topography of a surface of a substrate, particularly where the substrate has no sharp contrasts in material, crystallography, or angle.

It is an object of the invention to produce a method of determining the focusing conditions for an electron or an ion beam to focus the beam on a surface of a substrate, particularly where the substrate has no sharp contrasts in material, crystallography, or angle.

It is an object of the invention to produce a method of determining the depth of features in a generally flat, otherwise featureless surface.

It is an object of the invention to produce a method of determining features of sidewalls of a hole or trench in a substrate, particularly when the sidewall is sloped, vertical or undercut.

SUMMARY OF THE INVENTION

A focused particle bean, such as an electron, ion, atom, or molecular bean is directed on to the surface of a substrate. Scattered particles which travel in a straight line from the surface irradiated are collected in a particle detector. A particle blocking material having an edge is interposed between the surface and the particle detector, and the location of the shadow cast by the edge of the material is measured. The relative position of the surface and the edge casting the shadow can then be determined. Sweeping the particle beam can then be used to build up a topographic map of the surface. The depth and the sidewalls of holes and trenches are measured by appropriately changing the angle of incidence of the particle beam.

BRIEF DESCRIPTION OF THE DRAWINGS

FIG. 3A shows a side view sketch of a preferred embodiment of the invention.

FIG. 3B shows a graph of distance vs time for the embodiment sketched in FIG. 3A.

FIG. 4A shows a side view sketch of a preferred embodiment of the invention.

FIG. 4B shows a graph of distance vs time for the embodiment sketched in FIG. 4A.

FIG. 5A shows a side view sketch of a preferred embodiment of the invention.

FIG. 5B shows a sketch of the detector illumination for the embodiment sketched in FIG. 5A.

FIG. 6 shows a side view sketch of a preferred embodiment of the invention.

DETAILED DESCRIPTION OF THE INVENTION

Measurement of the topography of a surface by scanning electron microscope (SEM) is very difficult if the surface has no sharp differences in material, crystal directions, or surface angles. Often, the operators searches for a dust particle or other feature on the surface just to focus the beam on to the surface.

Figure 1A:
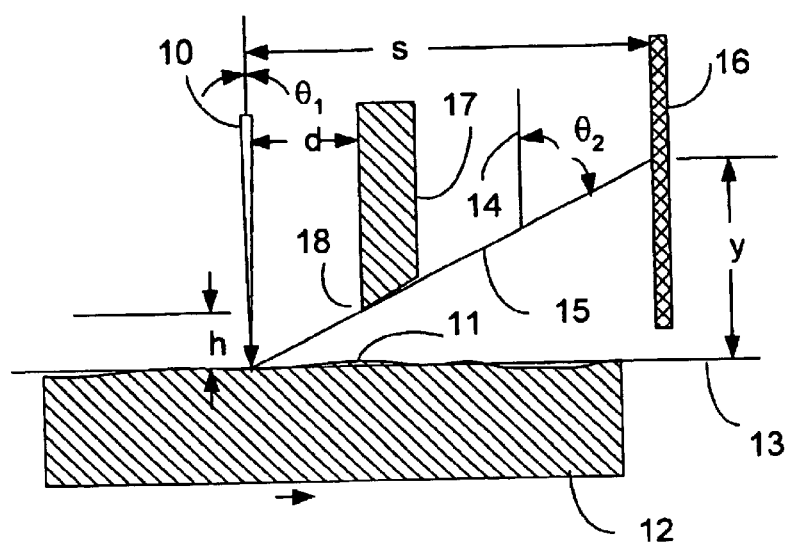
FIG. 1A shows a side view sketch of the most preferred embodiment of the invention.

The set up of the most preferred embodiment of the invention is shown in side view in FIG. 1A. A focused particle beam 10 is shown impinging on to a surface 11 of a substrate 12. The surface 11 as shown is not flat, but has a deviation from the flat plane 13 which is drawn as an "average" surface. The particle beam 10 is shown impinging normal to the plane 13, at an angle $\theta_1$ of $0°$ to the normal 14 to the plane 13. The particle beam 10 is most preferably a focused electron beam, but preferred embodiments of the invention use focused ion, atom, or molecular beams. Light beams (sometimes considered beams of quanta or particles) are specifically excluded as particles for the purposes of this specification. Particles 15 ejected from the surface 11 are shown flying in a straight line from the point of intersection of the particle beam 10 and the surface 11 to a particle detector 16. The particle detector 16 is a point detector, a line detector, or most preferably an array detector such as an imaging electron detector CCD or CMOS array. Backscattered or low energy loss, electrons having low energy loss (LLE)'s are the preferred particles 15 for the present invention. A body 17 opaque to particles 15 having an edge 18 is interposed between the point where the electron beam 10 impinges on the surface 11 and the detector 16. The body 17 casts a "shadow" on the detector 16, where the position of the shadow on the detector is determined by the relative positions of the intersection point and the edge 18. FIG. 1A shows the electrons at the edge of the shadow forming an angle $\theta_2$ to the normal 14. Simple geometry shows that $$\tan \theta_2 = d/h = s/y$$

and, if the distance h changes as the electron beam 10 is scanned, or alternatively, as the substrate 12 is translated perpendicular to the normal 14, then $$\Delta h = d/s \, \Delta y$$

Since d/s may be made very small, very small deviations $\Delta h$ lead to large values of $\Delta y$ which are easily measured by a number of pixel lines on an imaging detector.

Figure 1B:
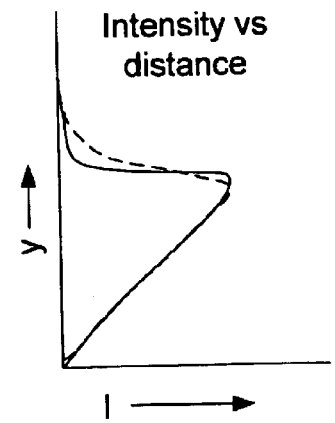
FIG. 1B shows a graph of distance vs intensity for the embodiment sketched in FIG. 1A.

FIG. 1B shows a graph of the instantaneous intensity vs distance of the response of an imaging detector 16 to the set up depicted in FIG. 1A. The intensity of backscattered electrons is proportional to $\sin^2 \theta_2$, and is very small for electrons scattered nearly parallel to the surface. If the electron beam 10 is focused on the surface 11, the solid line of FIG. 1B results. If the electron beam is focused above or below the surface, the dashed line provides a measure of the defocusing. Appropriate manipulation of the parameters of the electron beam 10, or raising or lowering the substrate 12 in the electron beam chamber, is used to focus the electron beam 10 on any particular surface element of the surface 11 by making the "edge" of the curve in FIG. 1B as sharp as possible.

Figure 2:
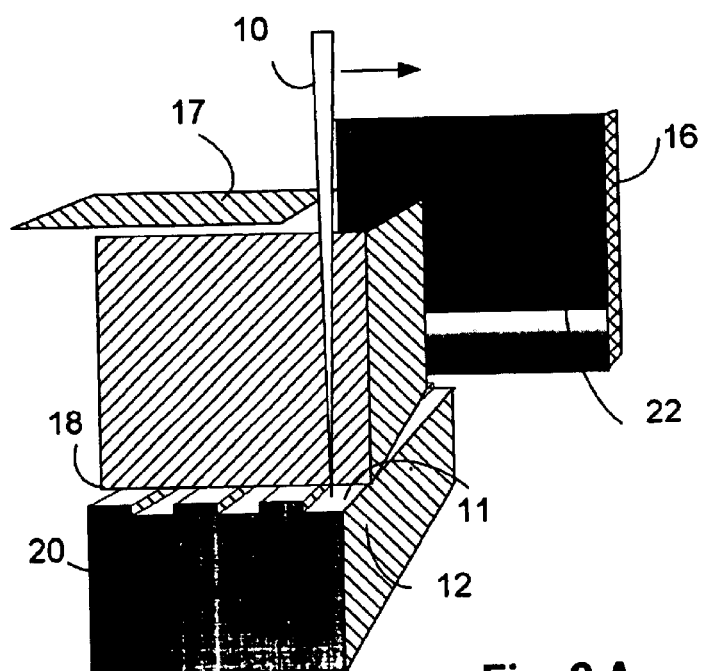
FIG. 2A shows a perspective sketch of a preferred embodiment of the invention.
FIG. 2B shows a graph of distance vs time for the embodiment sketched in FIG. 2A.
Figure 2B:
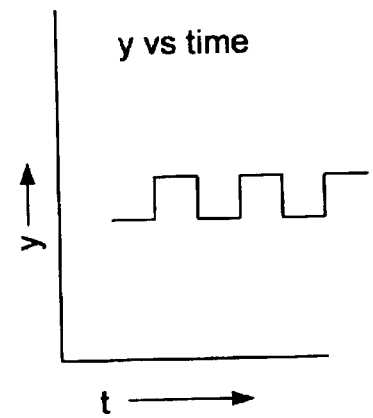

FIG. 2A shows a perspective sketch of a preferred embodiment of the invention. The electron beam 10 is shown scanning parallel to the edge 18 of the body 17 where the surface of the substrate 11 has a trench pattern with trenches 20 cut into the surface. The intensity of electrons on to the detector 16 is shown, as is the shadow line 22 from the edge 18 of the electron opaque material 17, at an instantaneous instant of time. The distance y measured by the shadow line on the electron detector is shown as a function of time in FIG. 2B for the scanning embodiment sketched in FIG. 2A. The depth of the trenches 20 is determined from the variations of y and the parameters h and d.

FIG. 3A shows a side view sketch of a preferred embodiment of the invention where the end elevation of a cut through the substrate 12 shows a trench 30 in the surface of the substrate. The focused electron beam 10 is shown impinging normal to the substrate, and sweeping at a constant rate perpendicular to the trench. The trench 30 has sloping sidewalls 32. FIG. 3B shows a graph of distance vs time for the embodiment sketched in FIG. 3A, where the slope angle and depth of the trench are calculable from the measurements of y.

FIG. 4A shows a side view sketch of a preferred embodiment of the invention where the end elevation of a cut through the substrate 12 shows a trench 40 in the surface of the substrate. The focused electron beam 10 is shown impinging at an angle $\theta_1$ to the substrate, and sweeping at a constant rate perpendicular to the trench. The trench 40 has vertical sidewalls 42. FIG. 4B shows a graph of distance vs time for the embodiment sketched in FIG. 4A, where a first sidewall angle, sidewall topography, and depth of the trench are calculable from the measurements of y. The graph is now not symmetric, because the scattered electrons are cut off from reaching the bottom of the trench by the edge of the other sidewall. To measure the other sidewall, the angle $\theta_1$ is reversed and the trench scanned again.

FIG. 5A shows a side view sketch of a preferred embodiment of the invention where the end elevation of a cut through the substrate 12 shows a trench 50 in the surface of the substrate. The focused electron beam 10 is shown impinging at an angle $\theta_1$ to the substrate. The trench 50 has undercut sidewalls 52. FIG. 5B shows an instantaneous sketch of the detector illumination for the embodiment sketched in FIG. 5A. The detector illumination is shadowed at 22 by the edge 18 as noted above, and also by the edges of the trench at 54 and 56. The shadows 54 and 56 also move as the electron beam sweeps across the trench.

FIG. 6 shows a side view sketch of a preferred embodiment of the invention, where the edge 63 of a trench 60 is used as an opaque block to the electrons to measure the topography of sidewall 62 and depth of the trench 60. As noted above, measurements of the position of the electron beam 10 with respect to the edge 63 of the trench are used to determine the topography of the sidewall from measurements of the distance of the y of the shadow of the edge of the trench and from the known dimensions of the relative positions of the electron beam with respect to the edge 63 of the trench and the detector 16.

Obviously, many modifications and variations of the present invention are possible in light of the above teachings. It is therefore to be understood that, within the scope of the appended claims, the invention may be practiced otherwise than as specifically described.

We claim:

1. A method of measurement of topographic features on a surface of a substrate, comprising:
   a) directing a focused beam of particles to fall at a first angle $\theta_1$ on to a first portion of the surface of the substrate, where $\theta_1$ is defined with respect to an average normal to the surface of the substrate;
   b) detecting particles emitted from the first portion of the surface of the substrate at a second angle $\theta_2$, where $\theta_2$ is defined with respect to the average normal to the surface of the substrate, the particles detected with a particle detector;
   c) interposing a particle opaque material between the first portion of the surface of the substrate and the particle detector, the particle opaque material having an edge;
   d) determining the relative position of the edge and the first portion of the surface of the substrate from the results of the detection of particles.

2. The method of claim 1, where the particles of the focused beam of particles are charged particles.

3. The method of claim 2, where the charged particles are electrons.

4. The method of claim 2, where the charged particles are ions.

5. The method of claim 1, where the particle opaque material is separate from the substrate.

6. The method of claim 5, further comprising:
   e) directing the focused beam of particles on to a plurality of portions of the surface of the substrate; then,
   f) determining the topographic features of the plurality of portions of the surface from the results of the detection of particles.

7. The method of claim 6, wherein the topographic features of the plurality of portions form a trench in the substrate, and wherein the trench and the edge form an angle significantly greater than 0°.

8. The method of claim 7, wherein the topographic features of the plurality of portions form a trench in the substrate, and wherein the trench and the edge form an angle approximately 90°.

9. The method of claim 8, wherein the trench in the substrate has sidewalls which are approximately parallel to the average normal to the surface of the substrate.

10. The method of claim 1, further comprising:
    e) repeating steps a–d with at least one of the angles $\theta_1$ and $\theta_2$ changed.

11. The method of claim 10, further comprising determining the parameters of the focused particle beam wherein the focused particle beam is focused on the surface of the substrate.

12. The method of claim 1, wherein the particle opaque material between the first portion of the surface of the substrate and the particle detector is a portion of the substrate.

13. The method of claim 12, further comprising:
    e) directing the focused beam of particles on to a plurality of portions of the surface of the substrate; then,
    f) determining the topographic features of the plurality of portions of the surface from the results of the detection of particles.

14. The method of claim 13, further comprising:
    e) repeating steps a–f with a change of the angle $\theta_1$.

15. The method of claim 13, wherein the plurality of portions of the surface of the substrate are portions of the surface of a trench in the substrate, and the edge is an edge of the trench.

* * * * *